(12) United States Patent
Puzo et al.

(10) Patent No.: US 8,153,610 B2
(45) Date of Patent: Apr. 10, 2012

(54) **SULFOGLYCOLIPID ANTIGENS, THEIR EXTRACTION FROM *MYCOBACTERIUM TUBERCULOSIS*, AND THEIR USE AGAINST TUBERCULOSIS**

(75) Inventors: Germain Puzo, Tolosane (FR); Martine Gilleron, Tolosane (FR); Steffen Stenger, Ulm (DE); Gennaro De Libero, Bottmingen (CH)

(73) Assignees: Centre National de la Recherche Scientifique (C.N.R.S.), Paris (FR); University Hospital of Basel, Basel (CH); University of Erlangen, Erlangen (DE)

( * ) Notice: Subject to any disclaimer, the term of this patent is extended or adjusted under 35 U.S.C. 154(b) by 1239 days.

(21) Appl. No.: 10/553,801

(22) PCT Filed: Apr. 9, 2004

(86) PCT No.: PCT/EP2004/003830
§ 371 (c)(1),
(2), (4) Date: Mar. 25, 2008

(87) PCT Pub. No.: WO2004/092192
PCT Pub. Date: Oct. 28, 2004

(65) Prior Publication Data
US 2008/0176818 A1  Jul. 24, 2008

(30) Foreign Application Priority Data
Apr. 18, 2003  (EP) .................................... 03290965

(51) Int. Cl.
*A61K 31/7016* (2006.01)
*C07H 13/06* (2006.01)
*A61P 31/06* (2006.01)

(52) U.S. Cl. .......... 514/53; 536/123.13; 435/29
(58) Field of Classification Search .......... 514/53; 536/123.13; 435/29, 435
See application file for complete search history.

(56) References Cited

OTHER PUBLICATIONS

Desmarais et al, J. Bacteriology, 1997, 3146-53.*
Vergne et al, Frontiers in Bioscience, 1998, 3, 865-76.*
Besra et al, Biochemistry, 1992, 31, 9832-37.*
The Merck Manual, 1992, pp. 140-141.*
I. Vergne, M. Daffe: "Interaction of mycobacterial glycolipids with host cells", Frontiers in Bioscience, vol. 3, 1998, pp. 856-876, XP008023822.

* cited by examiner

*Primary Examiner* — Shaojia Anna Jiang
*Assistant Examiner* — Ganapathy Krishnan
(74) *Attorney, Agent, or Firm* — Young & Thompson

(57) ABSTRACT

The present invention relates to compounds of the following general formula: (I) wherein $R_1$ and $R_2$ are fatty acyl groups, a process to extract them from *Mycobacterium tuberculosis*, and their use in the treatment or the prophylaxis of tuberculosis.

20 Claims, 4 Drawing Sheets

SULFOGLYCOLIPID ANTIGENS, THEIR EXTRACTION FROM *MYCOBACTERIUM TUBERCULOSIS*, AND THEIR USE AGAINST TUBERCULOSIS

The present invention relates to new sulfoglycolipid antigens, a process to extract them from *Mycobacterium tuberculosis*, and their use in the treatment or the prophylaxis of tuberculosis.

Each year, tuberculosis is the estimated cause of 3 million deaths. The causative agent of this disease is a bacterium, *Mycobacterium tuberculosis*, by which one of every three people is infected worldwide. It is transmitted through the air by sneezes or coughs of infected persons. The bacterium may be harboured in an inactive state by infected persons who will never develop the disease. However, under certain conditions, such as age or depression of the immune system, the bacterium may become active and cause the onset of tuberculosis.

It seems that the mycobacterial envelope accounts for an important part of the virulence of bacteria of the *Mycobacterium* genus. Indeed, up to 40% of mycobacteria dry weight is constituted by lipids. Among those lipids, some of them seem restricted to *Mycobacterium tuberculosis*, such as sulfoglycolipids for instance (Vergne I. and Daffe M. *Frontiers in Bioscience* (1998) 3:865-876). This family of glycolipids is typified by a sulfate substituent on position 2' of a trehalose unit (i.e. α-D-glucopyranosyl-(1-1')-α'-D-glucopyranoside) (A).

(A)

Members of the family differ from one another by the number, the position and the type of fatty acids substituted on the trehalose units. The fatty acids substituents notably comprise palmitic acid, stearic acid, phthioceranoic acid and hydroxyphthioceranoic acid. The latter two fatty acids are characteristic of sulfoglycolipids. The most abundant sulfoglycolipid is SL-I (Goren et al. *Biochemistry* (1976) 15:2728-2735) (B).

Its abundance has been shown to be correlated to strain virulence and it has been demonstrated that SL-I was able to inhibit macrophage antimicrobial activity and to block the effects of several inflammatory agents such as LPS, IFN-γ, or TNF-α on macrophages (Vergne I. and Daffe M. *Frontiers in Bioscience* (1998) 3:865-876).

At present, there are two ways of fighting tuberculosis: antibiotic therapy and vaccination.

The vaccine used for the prophylaxis of tuberculosis consists of a live attenuated bacterium of the *Mycobacterium bovis* species. It is named BCG, Bacillus of Calmette and Guerin, after the two scientists who first devised it, at the beginning of the 20$^{th}$ century. In addition to its flaw as being a live vaccine, which precludes its use in immunodepressed patients, its protection against tuberculosis is controversial. Thus, BCG protective efficacy in adults range from 0% to 80% according to varying studies, besides, it fails to protect against pulmonary tuberculosis, the most prevalent disease form in adults.

Moreover, antibiotic resistant strains of *M. tuberculosis* have been found in over 35 countries.

Hence, it is a subject of the present invention to provide a more effective way of treating and/or preventing tuberculosis.

It is a further subject of the invention to provide new immunogenic glycolipids extracted from *Mycobacterium tuberculosis*.

The invention notably provides new sulfoglycolipid antigens, specific of *M. tuberculosis*, which have been shown to stimulate CD1-restricted T lymphocytes in vitro.

The invention relates to compounds of the following general formula (I):

I wherein $R_1$ and $R_2$ are fatty acyl groups.

Fatty acyl groups are derived from fatty acid groups which have been esterified to the hydroxyl groups in position 2 and 3 of the trehalose-2'-sulfate unit.

Fatty acid groups are aliphatic carboxylic acids which can be linear or ramified, saturated or unsaturated, unsubstituted or substituted by groups such as hydroxyl, or ketone.

B

The invention particularly relates to compounds of formula I, wherein $R_1$ and $R_2$ independently from each other represent a fatty acyl group containing from 16 to 60 carbon atoms, and more particularly wherein $R_1$ and $R_2$ are selected from the group comprising:

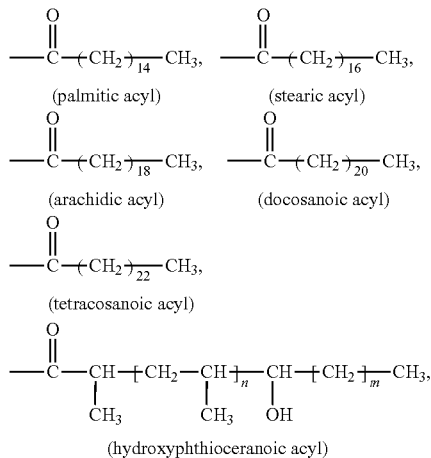

wherein m is 14 or 16 and n is an integer from 2 to 10,

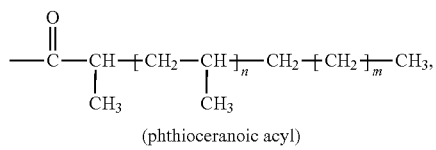

wherein m is 14 or 16 and n is an integer from 2 to 10,

The fatty acyl groups notably comprise linear and saturated fatty acyl groups such as groups according to formula —OC—$(CH_2)_k$—$CH_3$ wherein k is an integer from 14 to 58.

The invention more particularly relates to compounds of formula I, wherein $R_1$ and $R_2$ are selected from the group comprising palmitic acyl and stearic acyl, namely compounds of following formulae:

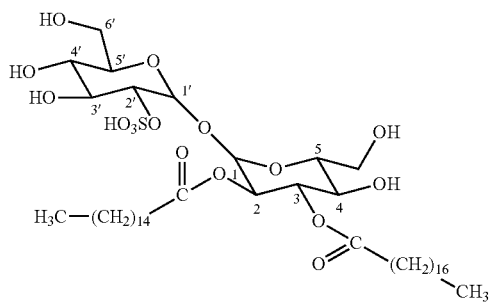

The invention further relates to compounds of formula I, wherein at least one of $R_1$ and $R_2$ represents a hydroxyphthioceranoic acyl group.

The invention more specifically relates to compounds of formula I, wherein $R_1$ or $R_2$ represents a hydroxyphthioceranoic acyl group.

The invention more particularly relates to compounds of formula I, wherein:

$R_1$ represents a hydroxyphthioceranoic acyl group, and $R_2$ represents a palmitic acyl group or a stearic acyl group, namely compounds of following formula (II):

II

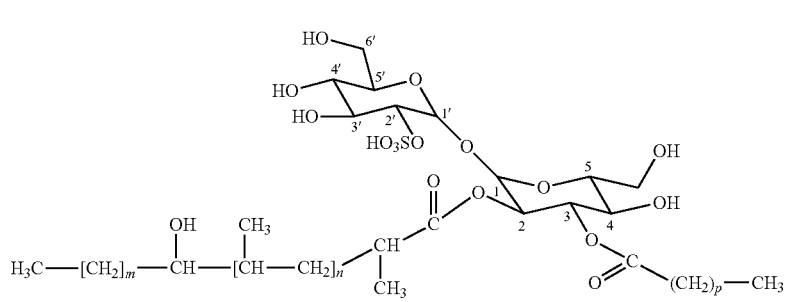

wherein p is 14 or 16, m is 14 or 16 and n is an integer from 2 to 10, or $R_2$ represents a hydroxyphthioceranoic acyl group, and $R_1$ represents a palmitic acyl group or a stearic acyl group, namely compounds of following formula (III):

III

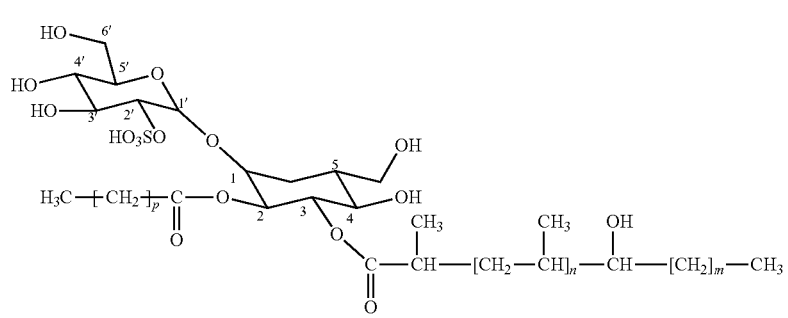

wherein p is 14 or 16, m is 14 or 16 and n is an integer from 2 to 10.

The invention relates in particular to compounds of formula II, wherein:

n=2, m=14 and p=14 (II.1);
n=2, m=14 and p=16 (II.2);
n=2, m=16 and p=14 (II.3);
n=2, m=16 and p=16 (II.4);
n=3, m=14 and p=14 (II.5);
n=3, m=14 and p=16 (II.6);
n=3, m=16 and p=14 (II.7);
n=3, m=16 and p=16 (II.8);
n=4, m=14 and p=14 (II.9);
n=4, m=14 and p=16 (II.10);
n=4, m=16 and p=14 (II.11);
n=4, m=16 and p=16 (II.12);
n=5, m=14 and p=14 (II.13);
n=5, m=14 and p=16 (II.14);
n=5, m=16 and p=14 (II.15);
n=5, m=16 and p=16 (II.16);
n=6, m=14 and p=14 (II.17);
n=6, m=14 and p=16 (II.18);
n=6, m=16 and p=14 (II.19);
n=6, m=16 and p=16 (II.20);
n=7, m=14 and p=14 (II.21);
n=7, m=14 and p=16 (II.22);
n=7, m=16 and p=14 (II.23);
n=7, m=16 and p=16 (II.24);
n=8, m=14 and p=14 (II.25);
n=8, m=14 and p=16 (II.26);
n=8, m=16 and p=14 (II.27);
n=8, m=16 and p=16 (II.28);
n=9, m=14 and p=14 (II.29);
n=9, m=14 and p=16 (II.30);
n=9, m=16 and p=14 (II.31);
n=9, m=16 and p=16 (II.32);
n=10, m=14 and p=14 (II.33);
n=10, m=14 and p=16 (II.34);
n=10, m=16 and p=14 (II.35);
n=10, m=16 and p=16 (II.36);

or of formula m, wherein:

n=2, m=14 and p=14 (III.1);
n=2, m=14 and p=16 (III.2);
n=2, m=16 and p=14 (III.3);
n=2, m=16 and p=16 (III.4);
n=3, m=14 and p=14 (III.5);
n=3, m=14 and p=16 (III.6);
n=3, m=16 and p=14 (III.7);
n=3, m=16 and p=16 (III.8);
n=4, m=14 and p=14 (III.9);
n=4, m=14 and p=16 (III.10);
n=4, m=16 and p=14 (III.11);
n=4, m=16 and p=16 (III.12);
n=5, m=14 and p=14 (III.13);
n=5, m=14 and p=16 (III.14);
n=5, m=16 and p=14 (III.15);
n=5, m=16 and p=16 (III.16);
n=6, m=14 and p=14 (III.17);
n=6, m=14 and p=16 (III.18);
n=6, m=16 and p=14 (III.19);
n=6, m=16 and p=16 (III.20);
n=7, m=14 and p=14 (III.21);
n=7, m=14 and p=16 (III.22);
n=7, m=16 and p=14 (III.23);
n=7, m=16 and p=16 (III.24);
n=8, m=14 and p=14 (III.25);
n=8, m=14 and p=16 (III.26);
n=8, m=16 and p=14 (III.27);
n=8, m=16 and p=16 (III.28);
n=9, m=14 and p=14 (III.29);
n=9, m=14 and p=16 (III.30);
n=9, m=16 and p=14 (III.31);
n=9, m=16 and p=16 (III.32);
n=10, m=14 and p=14 (III.33);
n=10, m=14 and p=16 (III.34);
n=10, m=16 and p=14 (III.35);
n=10, m=16 and p=16 (III.36);

The invention more specifically relates to compounds of following formulae:
III.21
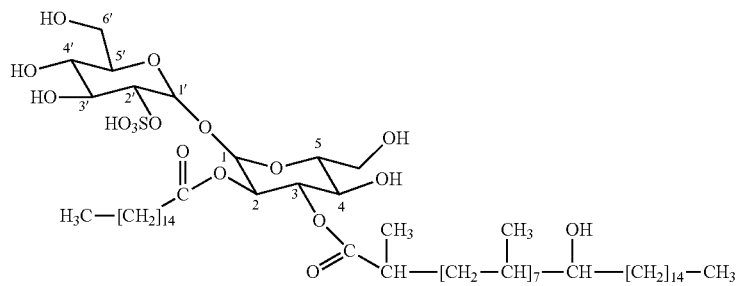
II.21
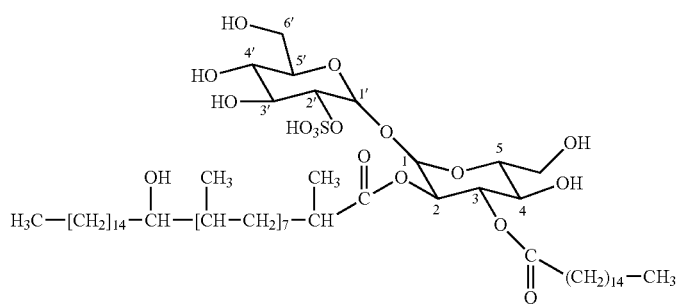
III.22
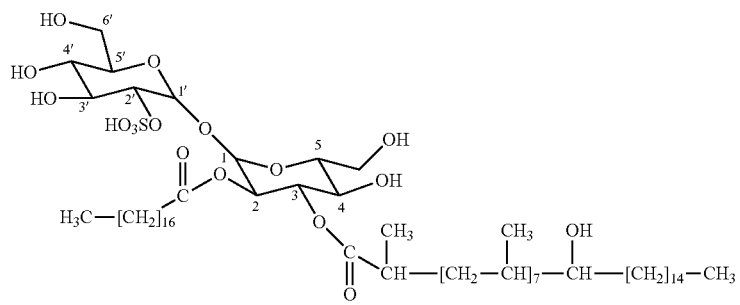
II.22
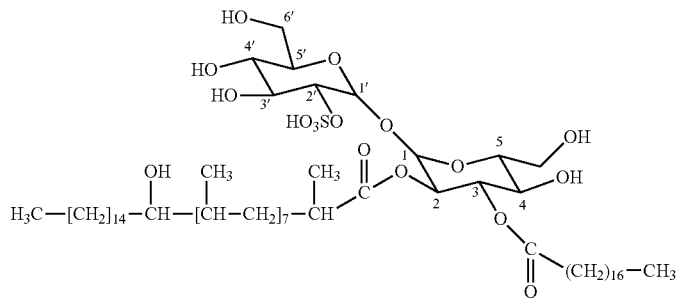
III.23
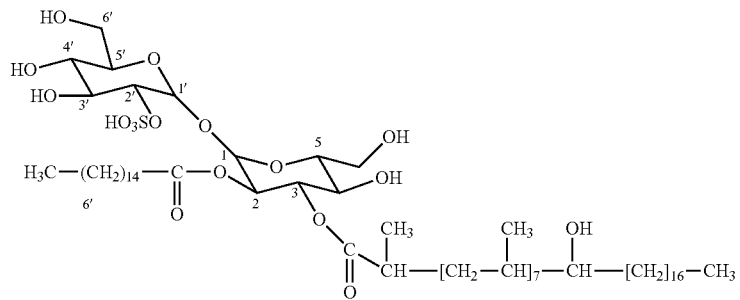

-continued

II.23

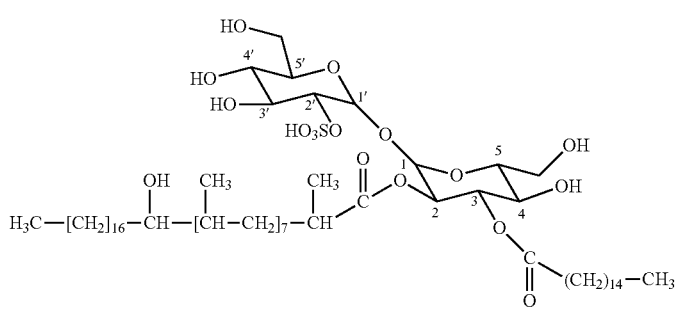

In a preferred embodiment, the invention relates to compounds of formulae III-21, III-22 or III-23.

According to another embodiment, the invention relates to a composition comprising at least two different compounds of formula I such as defined above.

The invention further relates to a composition characterized in that it comprises a mixture of compounds selected from the compounds of formulae II and III, preferably those of formulae II-1 to II-36 and of formulae III-1 to III-36, and more preferably those of formulae II-21, II-22, II-23, III-21, III-22 and III-23.

The invention also relates to a composition comprising a mixture of compounds selected from the compounds of formula III, preferably those of formulae III-1 to III-36, and more preferably those of formulae III-21, III-22 and III-23.

The invention relates in particular to a composition as defined above, wherein compounds selected from the compounds of formulae II-21, II-22, II-23, III-21, III-22 and III-23 represent from about 20% to about 100%, more particularly about 30%, of the total amount of compounds of formula I of said composition.

The invention also relates to a composition as defined above, wherein compounds selected from the compounds of formulae III-21, III-22 and III-23 represent from about 20% to about 100%, more particularly about 30%, of the total amount of compounds of formula I of said composition.

The invention notably relates to a composition as defined above, wherein at least one compound, selected from the list consisting of compounds of formulae II-21, II-22, II-23, III-21, III-22 and III-23, represents from about 20% to about 100%, notably 30% of the total amount of compounds of formula I of said composition.

The percentage used to characterize the contents of the above described compositions is a molar percentage.

The invention also relates to a pharmaceutical composition comprising at least one compound as defined above, or a composition as defined above, in association with a pharmaceutically acceptable vehicle.

A pharmaceutically acceptable carrier comprises in particular liposomes.

The composition may also comprise vaccine adjuvants. Vaccine adjuvants for use in human individuals or animals are well known to the man skilled in the art, a list of such salts can be found for instance in "A compendium of vaccine adjuvants and excipients" $2^{nd}$ edition, Vogel et al. Particular vaccine adjuvants notably comprise aluminum salts or M59, for example.

The invention particularly relates to a pharmaceutical composition as defined above, characterized in that it is presented in a form intended for administration by oral or injectable route.

The invention more particularly relates to a pharmaceutical composition as defined above, characterized in that it comprises one or more other products useful for the treatment or the prophylaxis of tuberculosis, such as BCG or mycobacterial proteins.

BCG stands for Bacillus of Calmette and Guerin, the different strains of BCG currently used for vaccination are notably described in Behr M. A. et al. *Science* (1999) 284:1520-1523.

The expression "mycobacterial proteins" refers to proteins, or fragments thereof, which are encoded by the genome of bacteria of the *Mycobacterium* genus and notably by the genome of *Mycobacterium tuberculosis*, such proteins may be advantageously recombinant. According to a preferred embodiment said mycobacterial proteins are antigens of *M. tuberculosis*.

Other products useful for the treatment or the prophylaxis of tuberculosis notably comprise immunomodulators, such as cytolines, DNA fragments encoding *M. tuberculosis* antigens, live *M. tuberculosis* deletion mutants, such as mutants in which virulence genes have been deleted, or live recombinant BCG, such as BCG expressing antigens of *M. tuberculosis*.

As used herein, tuberculosis refers to the disease caused in humans by the bacterium *Mycobacterium tuberculosis*, but also to the corresponding disease in animals.

According to another embodiment, the invention relates to products comprising:

at least one compound as defined above, and at least one other product useful for the treatment or the prophylaxis of tuberculosis, such as BCG or mycobacterial proteins, as a combined preparation for simultaneous, separate or sequential use in the treatment or the prophylaxis of tuberculosis.

The invention also relates to the use of at least one compound as defined above, or of an above mentioned composition, for the preparation of a medicament, notably a vaccine, intended for the treatment or the prophylaxis of tuberculosis.

Optionally the vaccine may comprise a vaccine adjuvant such as described above.

The invention relates to the use of at least one compound as defined above, or of a composition according as defined above, as an immune reaction activator, and more particularly an inflammatory reaction activator.

By "immune reaction activator" is meant a compound which has the ability to activate components or processes of the immune reaction, in vitro or in vivo, in particular cells of the immune system such as T lymphocytes, B lymphocytes, antigen presenting cells (APCs), such as dendritic cells or macrophages, monocytes or granulocytes.

By "inflammatory reaction activator" is meant a compound which has the ability to activate components or processes of the inflammatory reaction, in vitro or in vivo, such as diapedesis, capillary permeabilization, macrophage activation or fever onset for instance.

The invention also relates to the use of at least one compound as defined above, or of a composition as defined above, to induce the activation of T lymphocytes, notably CD1-restricted T lymphocytes. The activation can proceed in vitro or in vivo.

The activation of T lymphocytes can be assessed by several methods, such as measuring cell multiplication or cytokine production such as IFN-γ (interferon-γ), IL-2 (interleukine-2), IL-4 (interleukine-4), or TNF-α (tumor necrosis factor α), for instance.

CD1-restricted T lymphocytes are T lymphocytes which are activated by antigens presented by CD1 molecules.

The invention also relates to the use of at least one compound as defined above, or of a composition as defined above, to induce the production of IFN-γ, TNF-α, IL-4 or granulysin.

This production induction can be done in vitro or in vivo. The production of IFN-γ, TNF-α, IL-4 or granulysin can be measured for instance by immunoassays, such as ELISA (enzyme linked immunosorbent assay) or EIA (enzyme immunoassay).

According to another embodiment, the invention relates to a process for generating T cell clones, characterized in that it comprises the following stages:
  incubating antigen presenting cells (APCs), notably dendritic cells, with a *Mycobacterium tuberculosis* envelope preparation substantially devoid of proteins, to obtain non-protein envelope antigen loaded APCs,
  contacting peripheral blood mononuclear cells with the envelope antigen loaded APCs to obtain proliferating T cells,
  cloning proliferating T cells by limiting dilution and selecting the clones releasing a molecule selected from the group comprising IFN-γ, TNF-α, granulysin or IL-4 when contacted by envelope antigen loaded APCs to obtain T cell clones.

The invention further relates to T cell clones such as obtained by the abovementioned process. Such a T cell clone is described in the examples as Z4B27.

According to another embodiment, the invention relates to a process for screening products, such as sulfoglycolipids extracted from *Mycobacterium tuberculosis*, characterized in that it comprises the following stages:
  contacting dendritic cells loaded with the product to screen, notably sulfoglycolipids extracted from *Mycobacterium tuberculosis*, with the above-defined T cell clones,
  detecting a molecule selected from the group comprising IFN-γ, TNF-α, granulysin or IL-4, released by the T cell clones.

The invention also relates to a process for the extraction of compounds as defined above, or of a composition as defined above, from *Mycobacterium tuberculosis*, characterized in that it comprises the following stages:
  treatment of *M. tuberculosis* bacteria with a mixture of methanol and chloroform to obtain a chloroform/methanol extract,
  concentration of the chloroform/methanol extract followed by its partition between a chloroform phase and an aqueous phase,
  taking of the chloroform phase and evaporation of most of the chloroform, followed by addition of acetone thereto to obtain a precipitate and a soluble acetone phase,
  taking of the soluble acetone phase followed by its concentration, and application of the concentrated soluble acetone phase on a silicic acid column irrigated with mixtures of methanol and chloroform,
  elution of a fraction from the above-mentioned silicic acid column by a mixture of chloroform and approximately 20% methanol, said fraction corresponding to a composition as defined above,
  if necessary purification of the fraction eluted from the silicic acid column to obtain different preparations respectively containing substantially only one of the compounds as defined above.

EXAMPLE 1

Figure 1:
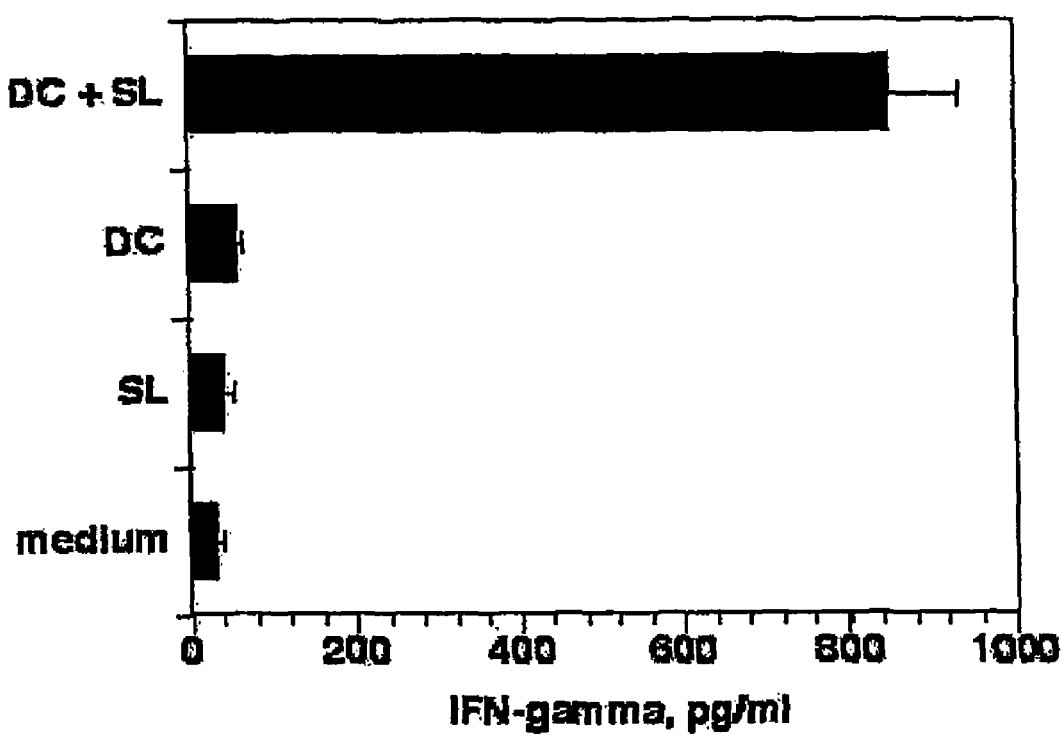
FIG. 1 represents the amount of IFN-γ (in pg/ml, horizontal axis) produced by T cell clone Z4B27 in response to stimulation (vertical axis) by the culture medium (medium), by sulfoglycolipids alone (SL), by dendritic cells alone (DC) or by dendritic cells loaded with sulfoglycolipids (DC+SL)
Figure 2:
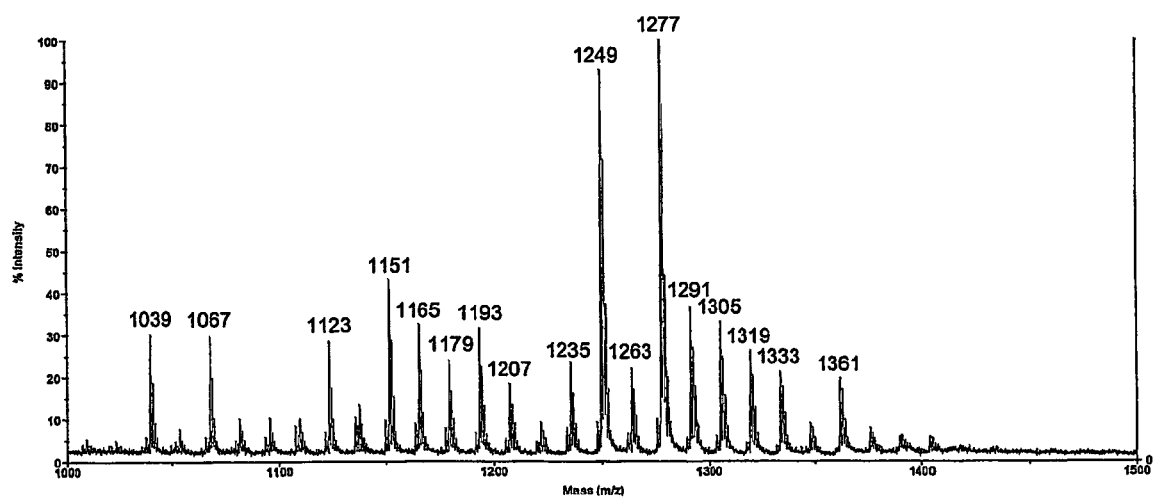
FIG. 2 represents the negative MALDI (Matrix Assisted Laser Desorption/Ionisation) mass spectrum of the purified preparation of sulfoglycolipids extracted from *M. tuberculosis* which activates the T-cell clone Z4B27. The horizontal axis represents the m/z ratio of the compounds contained in the preparation. The vertical axis represents the peak intensity as a percentage of maximum peak intensity. The major peaks are identified by their respective m/z ratio.

Generation of T Cell Clones Specific for *Mycobacterium Tuberculosis* Glycolipids 1. Preparation of Dendritic Cells Immature dendritic cells (DC) were prepared from peripheral blood of healthy donors. Plastic-adherent cells were cultured in RPMI-1640 medium containing 10% FCS (foetal calf serum), 50 ng/ml recombinant human GM-CSF, 1000 U/ml recombinant human IL-4, and were used after 5 days. Before each experiment the percentage of dendritic cells was monitored by immunofluorescence analysis using mAbs specific for CD1b (WM-25, Immunokontakt, Lugano, Switzerland), CD1a (OKT6) and CD1c (L161) (Instrumentation Laboratory, Schlieren, Switzerland) and was always >90%. For staining, cells were suspended in PBS containing 1% BSA and 0.04% $NaN_3$ and incubated with the primary mAbs (10 µg/ml) for 40 min, washed twice, and then further incubated with FITC-conjugated goat anti-mouse Ig for another 40 min at 4° C. After washing, cells were analyzed on a FACScan flow cytometer (Becton Dickinson).

2. Generation of Glycolipid-Specific T Cell Lines

Mycobacterial glycolipids were extracted from *Mycobacterium tuberculosis* cell wall. Killed cells were treated by a mixture of chloroform and methanol, 1/1, v/v and filtered, giving rise to delipidated cells and a supernatant containing cell wall glycolipids. The cells were extracted four times in the same way to yield a *M. tuberculosis* glycolipid extract.

T cell lines were established by culturing freshly isolated peripheral blood mononuclear cells (PBMC) with autologous DCs. DCs were incubated for 2 h with the above mentioned glycolipids (20 μg/ml) before addition of PBMCs. After 3 weeks, growing T cells were restimulated with heterologous DCs and the same preparation of glycolipids. An identical restimulation was performed after additional 3 weeks, cells were then tested for their antigen specificity.

3. Generation of Glycolipid-Specific T Cell Clones

T cells from glycolipid-specific T cell lines were cloned by limiting dilution in Terasaki plates. Cloning was performed using RPMI-1640 medium added with 5% human AB serum (Swiss Red Cross, Bern), 100 U/ml recombinant human IL-2, 1% PHA (Wellcome), 2 mM L-Glutamine (Gibco, 21051-024), 1 mM Na Pyruvate (Gibco, 11840-048), 1% Non-essential Aminoacids (Gibco, 11140-035), and 100 μg/ml Kanamycin (Gibco, 15160-021). Twelve days after plating, wells containing growing cells were scored and the plating efficiency was calculated according to Poisson's distribution. Cells were transferred into 96 wells plates and further expanded for one week before screening for their glycolipid specificity. The glycolipid specificity of T cell clones was detected by measuring the IFN-γ released in the supernatant 48 hr after stimulation with dendritic cells and glycolipids, using the human IFN-γ ELISA kit purchased from BD Phaminigen. The assay was performed using the protocol suggested by the dealer. Glycolipid-specific clones, such as Z4B27 (FIG. 1), were further expanded and characterized.

4. Characterization of Glycolipid-Specific T cell Clones

DC ($4\times10^4$/well in triplicate), in RPMI-1640 medium containing 10% FCS, were preincubated for 2 h at 37° C. with glycolipid antigen (1-50 μg/ml) before addition of T cells ($6\times10^4$/well). After 24-36 h of cultivation, TNF-α, IFN-γ and IL-4 released into culture supernatants were assayed by ELISA using commercial kits (Instrumentation Laboratory, Schlieren, Switzerland). CIR cells ($6\times10^4$/well in triplicate) transfected with CD1a, b, c, d or mock transfected were used in some assays.

Inhibition of T cell activation was performed by adding different doses of purified anti-CD3s TR66 mAb Fab fragments or purified anti-CD1b WM-25 mAbs together with glycolipid-pulsed APC. After 36 h, supernatants were harvested and tested in ELISA for the presence of TNF-α, IFN-γ and IL-4. Two of the glycolipid-specific T cell clones tested, Z4B26 and Z4B27, were found to be TCR $\alpha\beta^+$, $CD8^+$ and were restricted by CD1b. Clone Z4B27 was chosen in order to characterize the glycolipid antigens responsible for its activation.

EXAMPLE 2

Isolation and Characterization of Sulfoglycolipid Antigens of *Mycobacterium Tuberculosis* Activating T Cell Clones The specific antigens responsible for the activation of the Z4B27 T cell clone were searched for.

The above mentioned mycobacterial extract was concentrated and partitioned between water and chloroform. The chloroform phase contained most of the envelope lipids and glycolipids as well as the sulfoglycolipids. It was evaporated, and the residue was dissolved in the minimum of chloroform, then acetone was added and the mixture was kept overnight at 4° C. A precipitate was observed and by centrifugation at 4° C. for 15 min (3000×g) an "acetone-insoluble" phase and an "acetone-soluble" phase were obtained. Most of the sulfoglycolipids were found in the "acetone soluble" phase together with other lipids. The sulfoglycolipids were characterized by their behaviour on silica gel thin layer chromatography using chloroform/methanol, 9/1, v/v as migration solvent and were visualized with orcinol staining. In addition, their presence in the "acetone-soluble" phase was unambiguously established from MALDI-Time of Flight-mass spectrometry analysis (MALDI-Tof-MS) in negative mode. From the mass spectrum, recorded from 700 to 5000 mass units, mainly three families of sulfoglycolipids were characterized differing by their acylation degree and the fatty acyl appendage structures. The low mass range was mainly dominated by α-α-D-trehalose-2'-sulfate (A) containing two fatty acyl appendages including one hydroxyphthioceranoic acid residue (C) and either one palmitic ($HOOC—(CH_2)_{14}—CH_3$) or stearic acid ($HOOC—(CH_2)_{16}—CH_3$) residue. Beside this sulfoglycolipid, other acyl-forms were observed containing one and two additional hydroxyphthioceranoic acids corresponding to the two other sulfoglycolipids families noticed above.

A

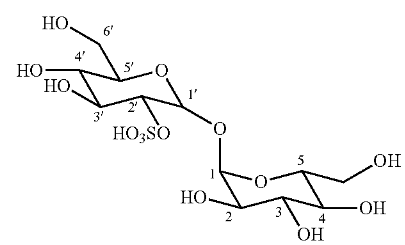

Trehalose-2'-sulfate

C

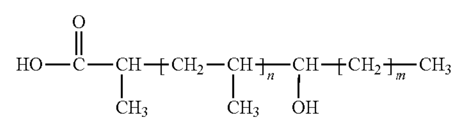

Hydroxyphthioceranoic acid

The "acetone-soluble" phase was then first fractionated on silicic acid column irrigated by chloroform, and chloroform containing 10, 20 and 30% of methanol. The bioactivity, i.e. the capacity to activate T cell clone Z4B27, was mainly restricted to the fraction eluted with a mixture of chloroform containing 20% of methanol.

MALDI-Tof-MS analysis showed that this fraction was composed by α-α-D-trehalose-2'-sulfate containing two fatty acyl appendages including hydroxyphthioceranoic acid residue with different chain lengths and either one palmitic or one stearic acid residue. FIG. 2 shows the MALDI-Tof spectrum recorded in negative mode using HABA [2-(4-hydroxyphenylazo)-benzoic acid] as matrix. The peaks were assigned to deprotonated molecular ions $(M-H)^-$ thus allowing the characterization of the different molecular species summarized in Table 1.

TABLE I

| Mass (m/z) | trehalose-2'-sulfate substituents |
|---|---|
| 1039 | Palmitic acid and hydroxyphthioceranoic acid (n = 2, m = 14) |
| 1067 | Stearic acid and hydroxyphthioceranoic acid (n = 2, m = 14), or palmitic acid and hydroxyphthioceranoic acid (n = 2, m = 16) |
| 1123 | Palmitic acid and hydroxyphthioceranoic acid (n = 4, m = 14) |
| 1151 | Stearic acid and hydroxyphthioceranoic acid (n = 4, m = 14) or palmitic acid and hydroxyphthioceranoic acid (n = 4, m = 16) |
| 1165 | Stearic acid and hydroxyphthioceranoic acid (n = 5 m = 16) |
| 1179 | Stearic acid and hydroxyphthioceranoic acid (n = 4 m = 16) |
| 1193 | Stearic acid and hydroxyphthioceranoic acid (n = 5 m = 14), or palmitic acid and hydroxyphthioceranoic acid (n = 5 m = 16) |
| 1207 | Palmitic acid and hydroxyphthioceranoic acid (n = 6 m = 14) |
| 1235 | Stearic acid and hydroxyphthioceranoic acid (n = 6 m = 14), or palmitic acid and hydroxyphthioceranoic acid (n = 6 m = 16) |
| 1249 | Palmitic acid and hydroxyphthioceranoic acid (n = 7 m = 14) |
| 1263 | Stearic acid and hydroxyphthioceranoic acid (n = 6 m = 16) |
| 1277 | Stearic acid and hydroxyphthioceranoic acid (n = 7 m = 14), or palmitic acid and hydroxyphthioceranoic acid (n = 7 m = 16) |
| 1291 | Palmitic acid and hydroxyphthioceranoic acid (n = 8 m = 14) |
| 1305 | Stearic acid and hydroxyphthioceranoic acid (n = 7 m = 16) |
| 1319 | Stearic acid and hydroxyphthioceranoic acid (n = 8 m = 14), or palmitic acid and hydroxyphthioceranoic acid (n = 8 m = 16) |
| 1333 | Palmitic acid and hydroxyphthioceranoic acid (n = 9 m = 14) |
| 1361 | Stearic acid and hydroxyphthioceranoic acid (n = 9 m = 14), or palmitic acid and hydroxyphthioceranoic acid (n = 9 m = 16) |

The desulfatation of the sulfoglycolipid antigens was performed and the bioactivity of the resulting glycolipids was investigated. The sulfoglycolipids (1 mg) dissolved in 1 ml of methanol were mixed with 50 mM of HCl at room temperature during 16 h. To the reaction mixture 3 ml of chloroform, 0.5 ml of methanol and 1 ml of 0.2% sodium acetate were added. The lower phase was washed with 2×2 ml of chloroform/methanol/water 3/48/47, v/v dried and tested on silica gel high performance thin layer chromatography plates. The glycolipids were visualized by orcinol staining and their migration using chloroform/methanol 9/1 as migration solvent was in agreement with the loss of the sulfate group. The desulfatation abrogated the capacity of the resulting glycolipid to activate the T cell clone Z4B27, revealing that sulfoglycolipids were the antigens which stimulate the T cell clones.

Finally, the fraction containing the diacylated α-α-D-trehalose-2'-sulfate antigens was applied on a C18 Sep-Pak cartridge which was successively irrigated with methanol/water 9/1, methanol and methanol/chloroform, 1/1, v/v. Using the bioassay, the bioactivity was restricted to the fractions eluted with methanol and methanol/chloroform, 1/1, v/v. These fractions analyzed by MALDI-Tof-MS in negative mode showed mass spectra allowing to assign the activity to the structure I: α-α-D-trehalose-2'-sulfate containing two fatty acyl appendages including one hydroxyphthioceranoic acid residue with different chain lengths and either one palmitic or one stearic acid residue.

Figure 3:
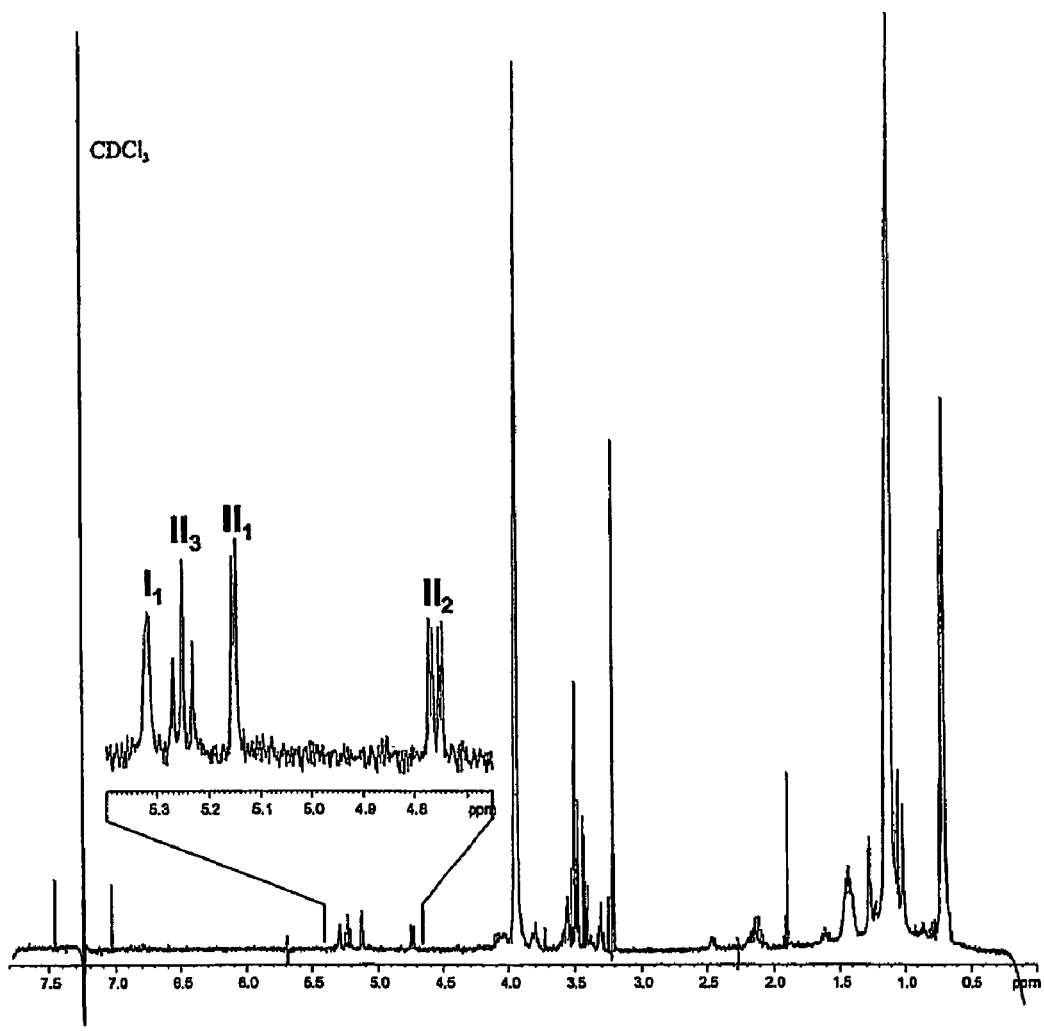
FIG. 3 represents the 1-D $^1$H NMR (Nuclear Magnetic Resonance) spectrum of the purified preparation of sulfoglycolipids extracted from *M. tuberculosis* which activates the T-cell clone Z4B27. The vertical axis represents the intensity of resonance and the horizontal axis the chemical shifts in ppm (parts per million). A close-up of the spectrum between 4.7 and 5.4 ppm is inserted in the left part of the spectrum. The peak designed as $CDCl_3$ corresponds the solvent.

From MALDI MS/MS experiments in positive mode, it was found that the two fatty acid residues were located on the same glucose unit (unit I) while the sulphate group was born by the other glucose moiety (unit II) composing the trehalose (see formula D). These data were supported by one and two dimensional $^1$H NMR experiments. FIG. 3 shows the one dimensional $^1$H spectrum. In the anomeric zone, four signals were observed namely $I_1$, $II_1$, $II_2$ and $II_3$. The resonances $I_1$ and $II_1$ typified the two anomeric protons of the α-α-trehalose core, and the resonances $II_2$ and $II_3$ were assigned to the H2 and H3 of the glucose moiety II, respectively. The downfield shifts of the H2 and H3 protons indicated that the fatty acyl appendages (hydroxyphthioceranoic acid and palmitic or stearic acids) were located on C2 and C3 of unit II. In addition, from the comparative analysis of the proton chemical shifts of the native sulfoglycolipid and its peracetylated derivative, the sulphate residue was located on the C2' of the glucose I moiety.

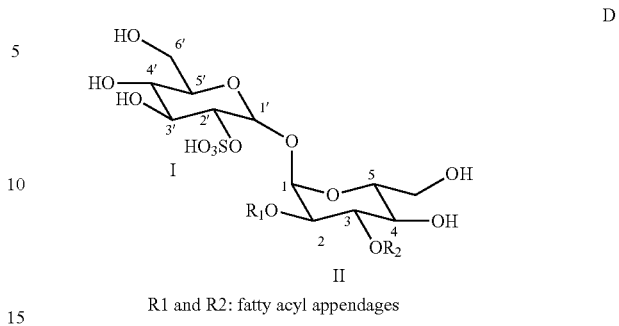

R1 and R2: fatty acyl appendages

EXAMPLE 3

Ex Vivo Assay of *Mycobacterium Tuberculosis* Sulfoglycolipids

To define the immunogenicity of sulfoglycolipids-antigens, IFN-γ release was measured after stimulation with the purified sulfoglycolipids. 2×10$^5$ PBMC per/well were incubated for 4 days in the presence of GM-CSF (500 U/ml) and IL-4 (5 ng/ml). Autologous effector T-cells were incubated in 10% human serum during this time. The sulfoglycolipids (10 μg/ml) were added to the irradiated, CD1-expressing antigen-presenting cells. Finally, effector cells were added (2×10$^5$/well) and IFN-γ release was measured by ELISA in the supernatants after 18 hours. The IFN-γ ELISA was performed in 96-well immunosorbent plates, which were coated with an IFN-γ capture antibody (2 μg/ml) overnight. Non-specific binding sites were blocked with PBS containing 1% bovine serum albumin. The supernatants were diluted 1:1 and added in a final volume of 100 μl. Plates were incubated at room temperature for 2 hours and removed by thorough washing (3-4 times). Finally, a biotinylated anti-IFN-γ antibody was added for 1 hour (2 μg/ml). For detection of immunoreactive IFN-γ, horseradish-peroxidase was added for 30 min. Finally, a chromogenic substrate (TMB, Endogen, Mass., USA) was added. After 20 min. incubation the reaction was stopped by the addition of sulfuric acid (2%). The intensity of the staining was determined photometrically at a wavelength of 480 nm. To estimate the concentration of cytokie in the supernatants, an IFN-γ standard with a known concentration was included in all tests. 82 PPD$^+$ donors (positive to the tuberculin test) and 54 PPD$^-$ donors (negative to the tuberculin test) were recruited and the response to the sulfoglycolipids was measured. Of the 82 PPD$^+$ donors 46 (56%) produced IFN-γ (range 72 to 798 pg/ml, sensitivity of the ELISA test: 15 pg/ml), as compared to only 4 control patients (7%).

To characterize the function of T cell clones, which recognize sulfoglycolipids, the expression of antibacterial effector molecules was measured and the antibacterial activity of dendritic cells (DC) infected with virulent *M. tuberculosis* was determined. To detect granulysin, sulfoglycolipids-reactive T cell clones were permeabilised using 0.5% saponin and a polyclonal rabbit serum directed against granulysin was added. Staining was visualized using a FITC-conjugated secondary antibody directed against rabbit immunoglobulins. The number of positive cells was quantitated by analyzing cells in a flow cytometer.

Figure 4:
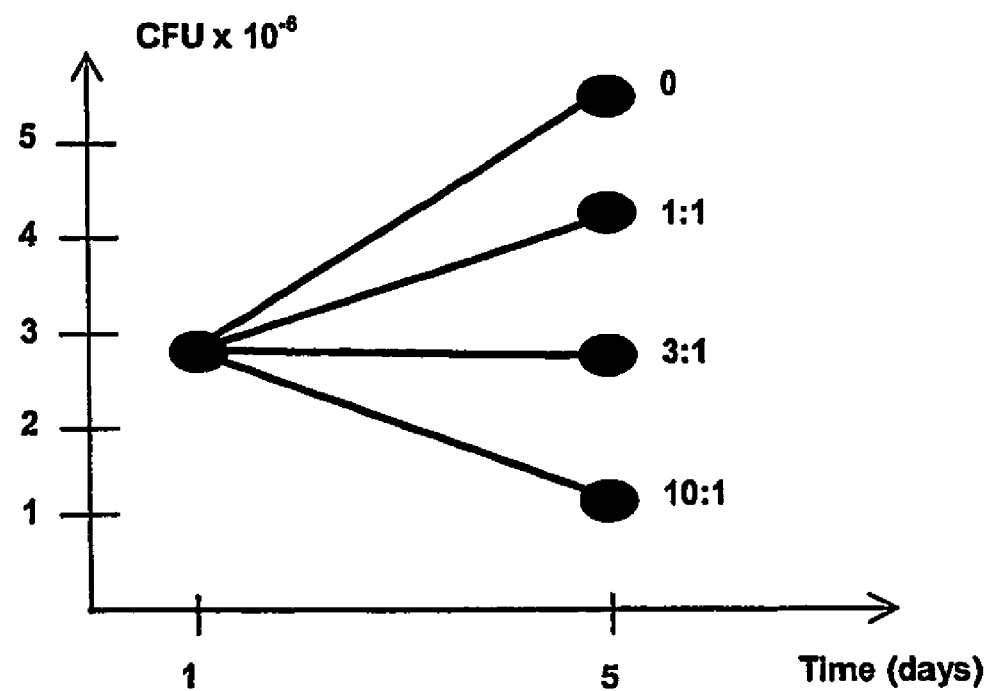
FIG. 4 represents a diagram showing the evolution of the number of *M. tuberculosis* CFUs (colony forming units) infecting dendritic cells ($\times 10^{-6}$, vertical axis) in response to the addition of increasing amounts of sulfoglycolipid specific T cell clones, represented as T cells:dendritic cells ratios on the right of the figure, between day 1 and day 5 of the experiment (horizontal axis).

For measuring the killing of *M. tuberculosis*, DCs were generated from peripheral blood monocytes by treatment with GM-CSF and IL-4. The cells were then infected with a virulent strain of *M. tuberculosis* (H37Rv) at a multiplicity of infection of 1. Non-phagocytosed bacteria were removed by thorough washing and then T-cells were added in increasing amounts as indicated in FIG. 4. The number of surviving bacteria was determined by plating cell lysates after 5 days of coincubation and counting the number of colonies grown after three weeks. Thus, it has been shown that T-cells specific for sulfoglycolipids recognize cells infected with live mycobacteria and—most importantly—kill the pathogen. Since sulfoglycolipids-responsive cells express granulysin, the secretion of this antibacterial molecule is most likely responsible for the killing of the pathogen. Therefore, sulfoglycolipids are presented on the surface of human host cells for mycobacteria recognition and killing.

Hence, a biochemically distinct and well characterized mycobacterial lipid antigen that is predominantly recognized by PPD$^+$ donors, but not by naxve controls, was identified. T-cell clones specific for sulfoglycolipids recognize DC infected with live *M. tuberculosis* bacilli and kill the pathogen possibly by the secretion of granulysin.

The invention claimed is:

1. A compound of the following general formula (I):

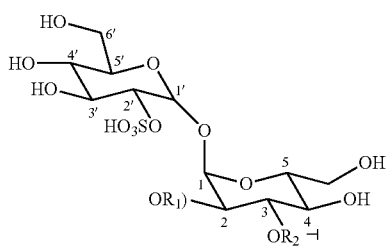

wherein $R_1$ and $R_2$ are fatty acyl groups selected from the group consisting of:

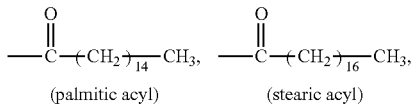

(palmitic acyl)  (stearic acyl)

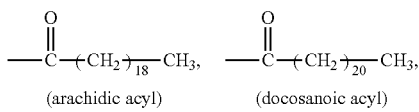

(arachidic acyl)  (docosanoic acyl)

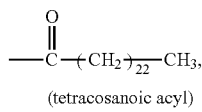

(tetracosanoic acyl)

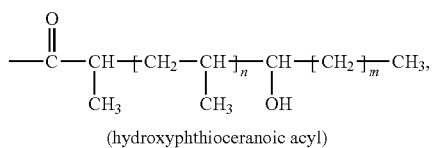

(hydroxyphthioceranoic acyl)

wherein m is 14 or 16 and n is an integer from 2 to 10.

2. The compound according to claim 1, wherein $R_1$ is palmitic acyl and $R_2$ is stearic acyl, and the compound has the formula:

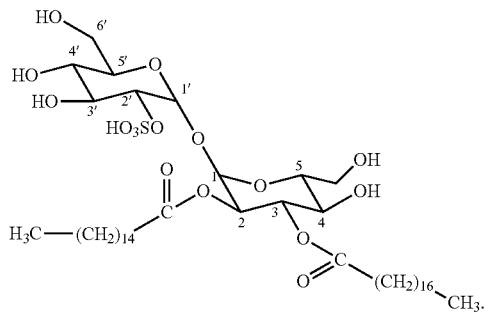

3. The compound according to claim 1, wherein at least one of $R_1$ and $R_2$ represents a hydroxyphthioceranoic acyl group.

4. The compound according to claim 1, wherein $R_1$ or $R_2$ represents a hydroxyphthioceranoic acyl group.

5. The compound according to claim 1, wherein: $R_1$ represents a hydroxyphthioceranoic acyl group, and $R_2$ represents a palmitic acyl group or a stearic acyl group, and the compound has the following formula (II):

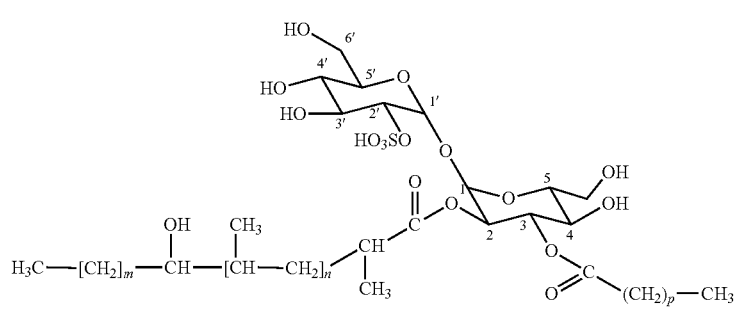

wherein p is 14 or 16, m is 14 or 16 and n is an integer from 2 to 10, or $R_2$ represents a hydroxyphthioceranoic acyl group, and $R_1$ represents a palmitic acyl group or a stearic acyl group, and the compound has the following formula (III):

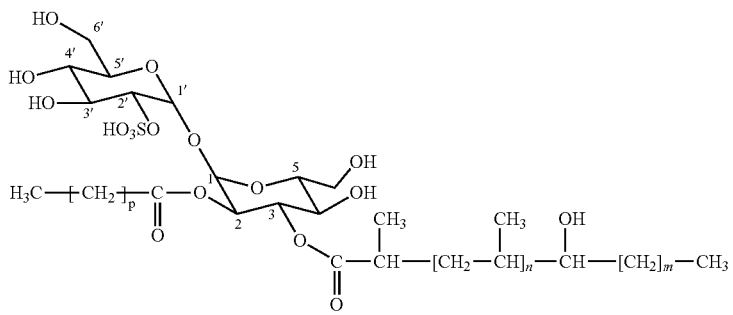

wherein p is 14 or 16, m is 14 or 16 and n is an integer from 2 to 10.

6. The compound according to claim 1, wherein the compound is of the following formula II,

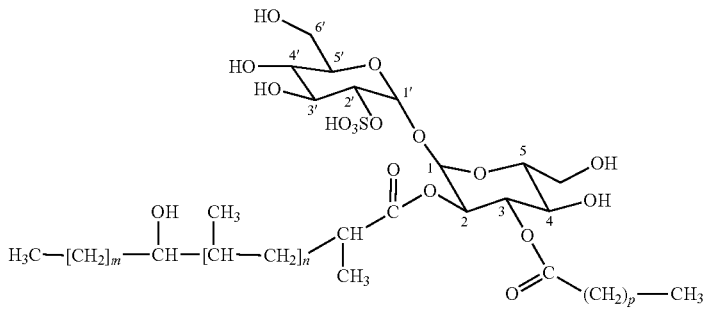

wherein the compound is selected from the group consisting of:

| | |
|---|---|
| n=2, m=14 and p=14 | (II.1); |
| n=2, m=14 and p=16 | (II.2); |
| n=2, m=16 and p=14 | (II.3); |
| n=2, m=16 and p=16 | (II.4); |
| n=3, m=14 and p=14 | (II.5); |
| n=3, m=14 and p=16 | (II.6); |
| n=3, m=16 and p=14 | (II.7); |
| n=3, m=16 and p=16 | (II.8); |
| n=4, m=14 and p=14 | (II.9); |
| n=4, m=14 and p=16 | (II.10); |
| n=4, m=16 and p=14 | (II.11); |
| n=4, m=16 and p=16 | (II.12); |
| n=5, m=14 and p=14 | (II.13); |
| n=5, m=14 and p=16 | (II.14); |
| n=5, m=16 and p=14 | (II.15); |
| n=5, m=16 and p=16 | (II.16); |
| n=6, m=14 and p=14 | (II.17); |
| n=6, m=14 and p=16 | (II.18); |
| n=6, m=16 and p=14 | (II.19); |
| n=6, m=16 and p=16 | (II.20); |
| n=7, m=14 and p=14 | (II.21); |
| n=7, m=14 and p=16 | (II.22); |
| n=7, m=16 and p=14 | (II.23); |
| n=7, m=16 and p=16 | (II.24); |
| n=8, m=14 and p=14 | (II.25); |
| n=8, m=14 and p=16 | (II.26); |
| n=8, m=16 and p=14 | (II.27); |
| n=8, m=16 and p=16 | (II.28); |
| n=9, m=14 and p=14 | (II.29); |
| n=9, m=14 and p=16 | (II.30); |
| n=9, m=16 and p=14 | (II.31); |
| n=9, m=16 and p=16 | (II.32); |
| n=10, m=14 and p=14 | (II.33); |
| n=10, m=14 and p=16 | (II.34); |
| n=10, m=16 and p=14 | (II.35); and |
| n=10, m=16 and p=16 | (II.36); | or of the following formula III,

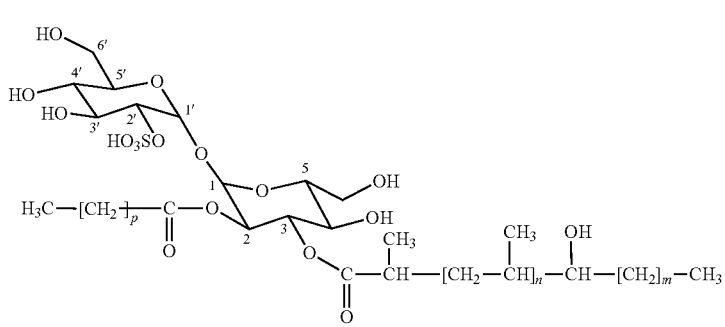

wherein the compound is selected from the group consisting of

| | |
|---|---|
| n=2, m=14 and p=14 | (III.1); |
| n=2, m=14 and p=16 | (III.2); |
| n=2, m=16 and p=14 | (III.3); |
| n=2, m=16 and p=16 | (III.4); |
| n=3, m=14 and p=14 | (III.5); |
| n=3, m=14 and p=16 | (III.6); |
| n=3, m=16 and p=14 | (III.7); |
| n=3, m=16 and p=16 | (III.8); |
| n=4, m=14 and p=14 | (III.9); |
| n=4, m=14 and p=16 | (III.10); |
| n=4, m=16 and p=14 | (III.11); |
| n=4, m=16 and p=16 | (III.12); |
| n=5, m=14 and p=14 | (III.13); |
| n=5, m=14 and p=16 | (III.14); |
| n=5, m=16 and p=14 | (III.15); |
| n=5, m=16 and p=16 | (III.16); |
| n=6, m=14 and p=14 | (III.17); |
| n=6, m=14 and p=16 | (III.18); |
| n=6, m=16 and p=14 | (III.19); |
| n=6, m=16 and p=16 | (III.20); |
| n=7, m=14 and p=14 | (III.21); |
| n=7, m=14 and p=16 | (III.22); |
| n=7, m=16 and p=14 | (III.23); |
| n=7, m=16 and p=16 | (III.24); |
| n=8, m=14 and p=14 | (III.25); |
| n=8, m=14 and p=16 | (III.26); |
| n=8, m=16 and p=14 | (III.27); |
| n=8, m=16 and p=16 | (III.28); |
| n=9, m=14 and p=14 | (III.29); |
| n=9, m=14 and p=16 | (III.30); |
| n=9, m=16 and p=14 | (III.31); |
| n=9, m=16 and p=16 | (III.32); |
| n=10, m=14 and p=14 | (III.33); |
| n=10, m=14 and p=16 | (III.34); |
| n=10, m=16 and p=14 | (III.35);and |
| n=10, m=16 and p=16 | (III.36). |

7. The compound according to claim 1, having a formula selected from the group consisting of:

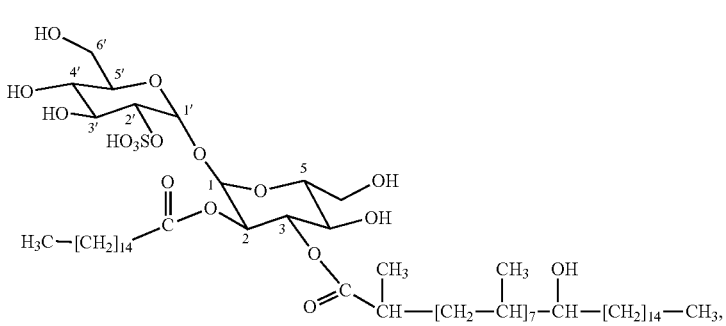

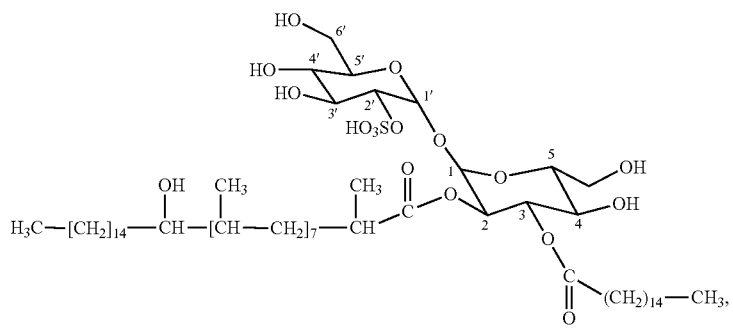
II.21
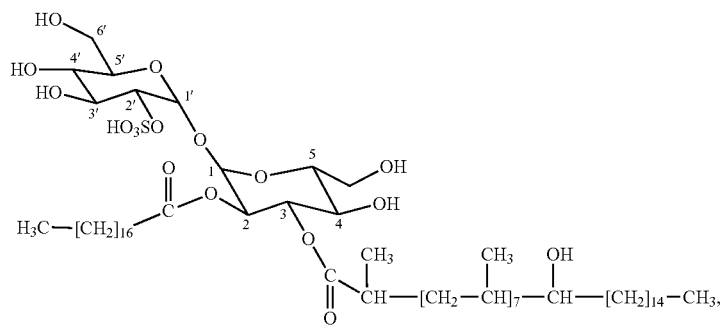
III.22
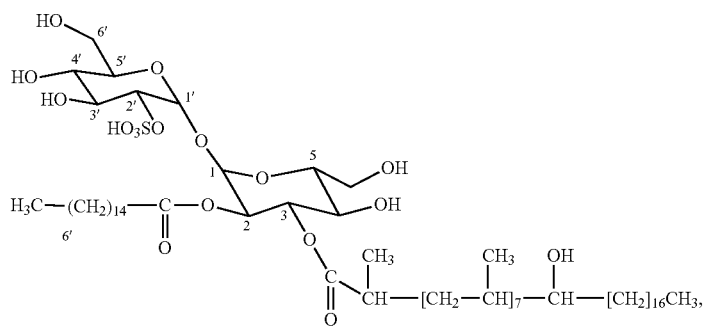
III.23
and
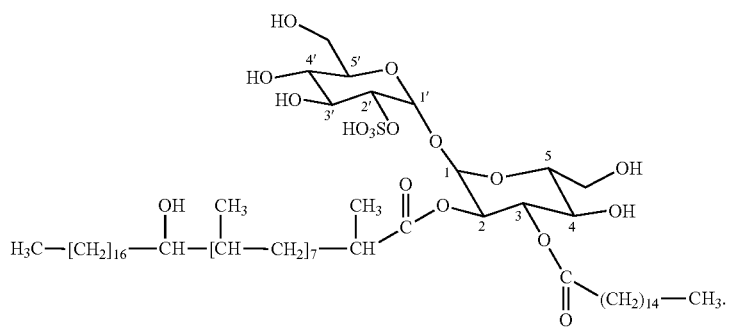
II.23
8. A composition comprising a mixture of at least two different compounds of formula I according to claim 1, wherein the at least two different compounds of formula (I) have different definitions for at least one of $R_1$ and $R_2$.

9. The composition according to claim 8, wherein the mixture of at least two different compounds is selected from (i) compounds according to formula (II):

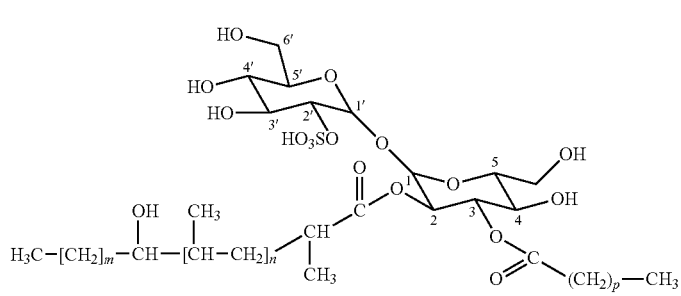

II wherein p is 14 or 16, m is 14 or 16 and n is an integer from 2 to 10, and the compounds differ by at least one of p, m or n or (ii) compounds according to formula (III):

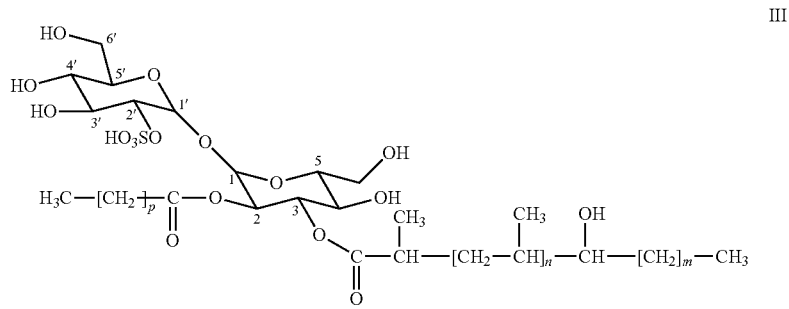

III wherein p is 14 or 16, m is 14 or 16 and n is an integer from 2 to 10, and the compounds differ by at least one of p, m or n.

10. The composition according to claim 8, wherein the mixture of at least two different compounds is:

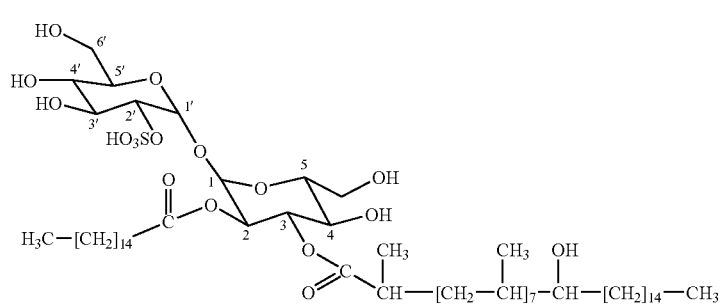

III.21

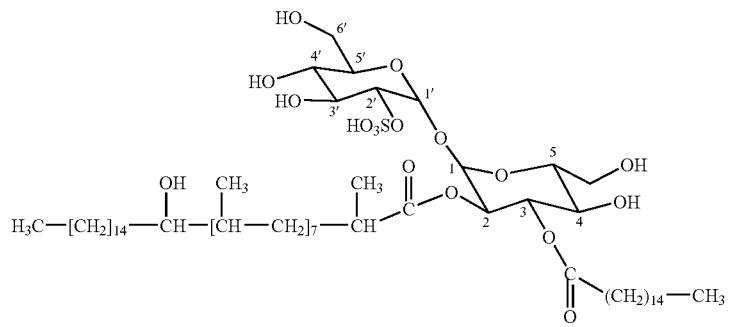
II.21
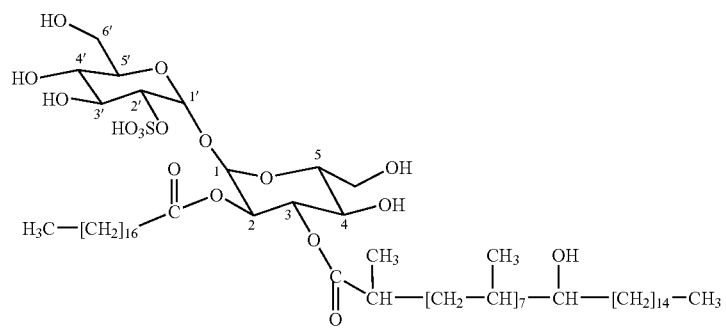
III.22
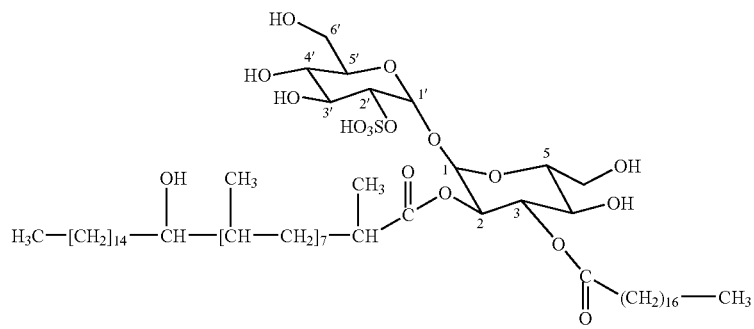
II.22
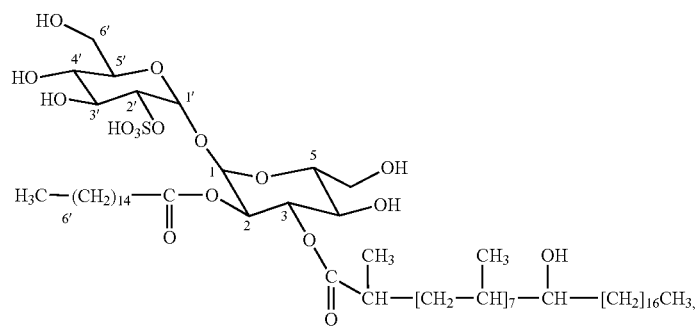
III.23
and

-continued

II.23

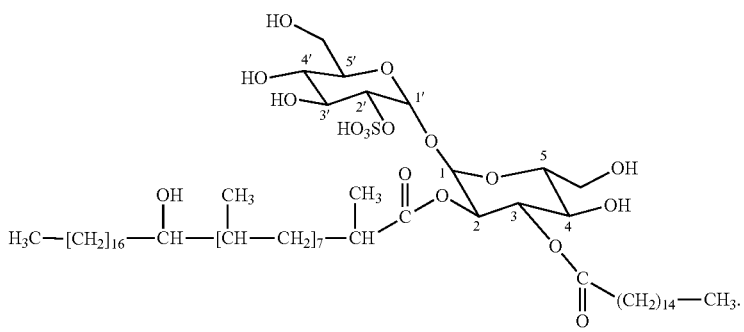

11. The composition according to claim 10, wherein the compounds represent from about 20% to about 100% of the total amount of compounds of formula I of said composition.

12. An immunogenic composition comprising at least one compound of claim 1, in association with a pharmaceutically acceptable vehicle.

13. The immunogenic composition according to claim 12, the immunogenic composition is presented in a form intended for administration by oral or injectable route.

14. The immunogenic composition according to claim 12, further comprising one or more products selected from the group consisting of cytokines, DNA fragments encoding *M. tuberculosis* antigens, live *M. tuberculosis* deletion mutants and live recombinant Bacillus of Calmette and Gerinor.

15. A product comprising:

at least one compound according to claim 1, and at least one product selected from the group consisting of cytokines, DNA fragments encoding *M. tuberculosis* antigens, live *M. tuberculosis* deletion mutants and live recombinant Bacillus of Calmette and Gerinor, as a combined preparation for simultaneous, separate or sequential administration with said at least one compound.

16. A method for the treatment of tuberculosis, comprising the administration of a therapeutically effective amount to a patient of at least one compound according to claim 1.

17. A method of activating immune reaction, comprising the administration of a therapeutically effective amount to a patient of at least one compound according to claim 1.

18. A method of inducing the activation of T lymphocytes, comprising the administration of a therapeutically effective amount to a patient of at least one compound according to claim 1.

19. A method of inducing the production of IFN-γ, INF-α, IL-4 or granulysin, comprising the administration of a therapeutically effective amount to a patient of at least one compound according to claim 1.

20. A process for the extraction of the compound of claim 1, from *Mycobacterium tuberculosis*, comprising the following stages:

(a) treating *M. tuberculosis* bacteria with a mixture of methanol and chloroform to obtain a chloroform/methanol extract, (b) concentrating the chloroform/methanol extract followed by its partition between a chloroform phase and an aqueous phase, (c) taking of the chloroform phase and evaporation of most of the chloroform, followed by adding acetone thereto to obtain a precipitate and a soluble acetone phase, (d) taking of the soluble acetone phase followed by concentration, and applying the concentrated soluble acetone phase on a silicic acid column irrigated with mixtures of methanol and chloroform, (e) eluting a fraction from the above-mentioned silicic acid column by a mixture of chloroform and approximately 20% methanol, and, optionally, (f) purifying the fraction eluted from the silicic acid column to obtain different preparations respectively containing substantially only one compound.

* * * * *